(12) United States Patent
Chen et al.

(10) Patent No.: US 6,667,309 B2
(45) Date of Patent: Dec. 23, 2003

(54) CYCLOBUTENE DERIVATIVES USEFUL AS ANTAGONISTS OF THE MOTILIN RECEPTOR

(75) Inventors: Robert H. Chen, Belle Mead, NJ (US); Min A. Xiang, Bridgewater, NJ (US)

(73) Assignee: Ortho-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 10/095,981

(22) Filed: Mar. 12, 2002

(65) Prior Publication Data

US 2002/0103238 A1 Aug. 1, 2002

Related U.S. Application Data

(62) Division of application No. 09/803,565, filed on Mar. 9, 2001, now Pat. No. 6,384,031.
(60) Provisional application No. 60/188,919, filed on Mar. 13, 2000.

(51) Int. Cl.$^7$ .................... A61K 31/535; C07D 265/30
(52) U.S. Cl. .............. 514/237.8; 514/255.01; 514/329; 514/357; 544/165; 544/382; 546/223; 546/316
(58) Field of Search ................. 544/165, 382; 546/223, 316; 514/237.8, 255.01, 329, 357

(56) References Cited

U.S. PATENT DOCUMENTS

| 5,086,053 A | 2/1992 | Brodin et al. |
| 5,824,678 A | 10/1998 | Harrison et al. |
| 5,972,939 A | 10/1999 | Chen et al. |

*Primary Examiner*—Joseph K. McKane
*Assistant Examiner*—Sonya Wright

(57) ABSTRACT

The compounds of formula I are useful in treating gastrointestinal disorders associated with antagonizing the motilin receptor. The compounds compete with erythromycin and motilin for the motilin receptor. In addition the compounds are antagonists of the contractile smooth muscle response to those ligands.

10 Claims, No Drawings

CYCLOBUTENE DERIVATIVES USEFUL AS ANTAGONISTS OF THE MOTILIN RECEPTOR

CROSS REFERENCE TO RELATED APPLICATIONS

This application is a divisional of prior application Ser. No. 09/803,565, filed Mar. 9, 2001, now U.S. Pat. No. 6,384,031 which claims benefit of provisional application 60/188,919 filed Mar. 13, 2000, the contents of which are hereby incorporated by reference.

FIELD OF THE INVENTION

This invention relates to a series of novel cyclobutene derivatives, pharmaceutical compositions containing them and intermediates used in their manufacture. The compounds of the invention are useful as non-peptidyl antagonists of the motilin receptor. In addition, the compounds display efficacy and potency which are comparable to known motilin and erythromycin antagonists.

BACKGROUND

In mammals, the digestion of nutrients and the elimination of waste is controlled by the gastrointestinal system. This system is, to say the least, complicated. There are a number of natural peptides, ligands, enzymes, and receptors which play a vital role in this system and are potential targets for drug discovery. Modifying the production of, or responses to these endogenous substances can have an effect upon the physiological responses such as diarrhea, nausea, and abdominal cramping. One example of an endogenous substance which affects the gastrointestinal system is motilin.

Motilin is a peptide of 22 amino acids which is produced in the gastrointestinal system of a number of species. Although the sequence of the peptide varies from species to species, there are a great deal of similarities. For example, human motilin and porcine motilin are identical; while motilin isolated from the dog and the rabbit differ by five and four amino acids, respectively. Motilin induces smooth muscle contractions in the stomach tissue of dogs, rabbits, and humans as well as in the colon of rabbits. Apart from local gastrointestinal intestinal tissues, motilin and its receptors have been found in other tissues. For example, motilin has been found in circulating plasma, where a rise in the concentration of motilin has been associated with gastric effects which occur during fasting in dogs and humans (Itoh, Z. et al., 1976, *Scand. J. Gastroenterol.* 11:93–110; Vantrappen, G. et al. *Dig.,* 1979, *Dis Sci* 24,497–500). In addition, when motilin was intravenously administered to humans it was found to increase gastric emptying and gut hormone release (Christofides, N. D. et al., 1979, *Gastroenterology* 76:903–907).

Aside from motilin itself, there are other substances which are agonists of the motilin receptor and which elicit gastrointestinal emptying. One of those agents is the antibiotic erythromycin. Even though erythromycin is a useful drug, a great number of patients are affected by the drug's gastrointestinal side effects. Studies have shown that erythromycin elicits biological responses that are comparable to motilin itself and therefore may be useful in the treatment of diseases such as chronic idiopathic intestinal pseudo-obstruction and gastroparesis (Weber, F. et al., 1993, *The American Journal of Gastroenterology,* 88:4, 485–90).

Although motilin and erythromycin are agonists of the motilin receptor, there is a need for antagonists of this receptor as well. The nausea, abdominal cramping, and diarrhea which are associated with motilin agonists are not always welcome physiological events. The increased gut motility induced by motilin has been implicated in diseases such as Irritable Bowel Syndrome and esophageal reflux. Therefore researchers have been searching for motilin antagonists.

One such antagonist is OHM-11526. This is a peptide derived from porcine motilin which competes with both motilin and erythromycin for the motilin receptor in a number of species, including rabbits and humans. In addition, this peptide is an antagonist of the contractile smooth muscle response to both erythromycin and motilin in an in vitro rabbit model (Depoortere, I. et al., 1995, *European Journal of Pharmacology,* 286, 241–47). Although this substance is potent in that model, it is a peptide and as such it is susceptible to the enzymes of the digestive tract (Zen Itoh, *Motilin,* xvi, 1990). Therefore it is desirable to find other agents which are not peptides as potential motilin antagonists. The compounds of this invention are such agents.

U.S. Pat. No. 5,972,939 to Chen et al. describes cyclopentene derivatives which are useful in treating gastrointestinal disorders associated with antagonizing the motilin receptor.

SUMMARY OF THE INVENTION

The present invention is directed to compounds of Formula I

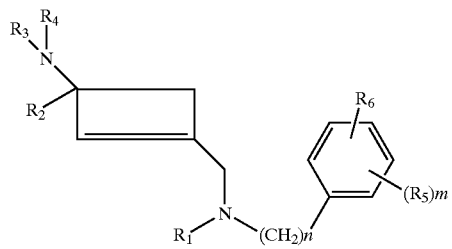

wherein

R$_1$ is selected from hydrogen, C$_{1-5}$alkyl optionally substituted with halogen, aminoC$_{1-5}$alkyl, C$_{1-5}$alkylaminoC$_{1-5}$alkyl, di-C$_{1-5}$alkylaminoC$_{1-5}$alkyl, C$_{1-5}$alkylcarbonyl, C$_{1-5}$alkoxycarbonyl, aminocarbonyl, C$_{1-9}$alkylaminocarbonyl, cycloC$_{3-9}$alkylaminocarbonyl, heteroarylaminocarbonyl optionally substituted with one or more C$_{1-5}$alkyl, pyridinylcarbonyl optionally substituted with one or more substituents selected from the group consisting of halogen and C$_{1-5}$alkyl, thiophenecarbonyl optionally substituted with one or more substituents selected from the group consisting of halogen and C$_{1-5}$alkyl, phenyl, phenylC$_{1-5}$alkyl, phenoxycarbonyl, phenylcarbonyl, diphenylmethylcarbonyl, phenylaminocarbonyl, phenylthiocarbonyl, phenylaminothiocarbonyl, said phenyl, phenylC$_{1-5}$alkyl, phenoxycarbonyl, phenylcarbonyl, diphenylmethylcarbonyl, phenylaminocarbonyl, phenylthiocarbonyl, phenylaminothiocarbonyl being optionally substituted with one or more substituents selected from the group consisting of halogen, C$_{1-5}$alkyl, trihalomethyl, C$_{1-5}$alkoxy, amino, nitrile, nitro, C$_{1-5}$alkylamino, and di-C$_{1-5}$alkylamino, which substituents may be taken together to form a fused bicyclic aromatic ring or taken together with the phenyl ring to form a fused bicyclic 7–10 membered heterocyclic ring having one or two heteroatoms selected from oxygen, sulfur and nitrogen, and R$_a$R$_b$N—C$_{1-5}$alkyl wherein R$_a$ and R$_b$ are independently selected from hydrogen and C$_{1-5}$alkyl, or taken together to form a morpholine, piperazine, piperidine, or N-substituted piperidine wherein the N-substitutent is C$_{1-5}$alkyl or phenylC$_{1-5}$alkyl;

R$_2$ is selected from hydrogen, C$_{1-5}$alkyl, C$_{1-5}$alkoxy, phenyl optionally substituted with one or more substituents selected from the group consisting of halogen and C$_{1-5}$alkyl, and phenylC$_{1-5}$alkyl optionally substituted with one or more substituents selected from the group consisting of halogen, C$_{1-5}$alkyl, C$_{1-5}$alkoxy, halo and di-C$_{1-5}$alkylamino;

R$_3$ is selected from hydrogen, C$_{1-5}$alkylcarbonyl optionally substituted with halogen, and phenylcarbonyl optionally substituted with one or more substituents selected from the group consisting of halogen, C$_{1-5}$alkyl, C$_{1-5}$alkoxy, amino, C$_{1-5}$alkylamino, and di-C$_{1-5}$alkylamino;

R$_4$ is selected from hydrogen, C$_{1-5}$alkyl, C$_{1-5}$alkylcarbonyl optionally substituted with halogen, and phenylcarbonyl optionally substituted with one or more substituents selected from the group consisting of halogen, C$_{1-5}$alkyl, C$_{1-5}$alkoxy, amino, C$_{1-5}$alkylamino, and di-C$_{1-5}$alkylamino;

n is 0–3;

m is 1–5;

R$_5$ is

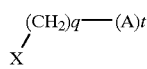

wherein:

q is 0–3;

t is 0–1;

X is oxygen, CH$_2$, sulfur, hydroxy, thiol, or NR$_c$ wherein

R$_c$ is selected from hydrogen, C$_{1-5}$alkyl, morpholinoC$_{1-5}$alkyl, piperidinylC$_{1-5}$alkyl, N-phenylmethylpiperidinyl, and piperazinylC$_{1-5}$alkyl, with the proviso that if q and t are 0, X is hydroxy, thiol, or amino;

A is C$_{1-5}$alkoxycarbonyl, phenylcarbonyl, or R$_7$R$_8$N— wherein wherein R$_7$ and R$_8$ are independently selected from hydrogen, C$_{1-5}$alkyl, and cycloC$_{1-9}$alkyl, or R$_7$ and R$_8$ form a 5- or 6-membered heterocyclic ring with one or more heteroatoms selected from the group consisting of oxygen, nitrogen, sulfur, and sulfoxides and N-oxides thereof; and R$_6$ is selected from hydrogen, halogen, C$_{1-5}$alkoxy, C$_{1-5}$alkylamino, and di-C$_{1-5}$alkylamino; or a pharmaceutically acceptable salt thereof.

The compounds of Formula I are useful in treating gastrointestinal disorders associated with the motilin receptor. The compounds compete with erythromycin and motilin for the motilin receptor. In addition, the compounds are antagonists of the contractile smooth muscle response to those ligands.

The present invention also comprises pharmaceutical compositions containing one or more of the compounds of Formula I as well as methods for the treatment of disorders related to the gastrointestinal system which are associated with the motilin receptor. Such diseases include Irritable Bowel Syndrome, esophageal reflux, and the gastrointestinal side effects of erythromycin.

DETAILED DESCRIPTION OF THE INVENTION

The terms used in describing the invention are commonly used and known to those skilled in the art. However, the terms that could have other meanings are defined. "Independently" means that when there are more than one substituent, the substituents may be different. The term "alkyl" refers to straight, cyclic and branched-chain alkyl groups and "alkoxy" refers O-alkyl where alkyl is as defined supra. The symbol "Ph" refers to phenyl, the term "fused bicyclic aromatic" includes fused aromatic rings such as naphthyl and the like. The symbol "Ph" refers to phenyl. "Halogen" or "halo" means F, Cl, Br, and I. The term "fused bicyclic heterocycle" includes benzodioxoles and the like. The term "heteroaryl" means a stable five or six membered monocyclic aromatic ring system which consists of carbon atoms and from one to three heteroatoms selected from N, O or S. The heteroaryl group may be attached at any heteroatom or carbon atom which results in the creation of a stable structure. Examples of heteroaryl groups include, but are not limited to, triazole, thiazole, thiadiazole, oxazole, imidazole, pyrazole, pyrimidine, isothiazole, isoindole, isoxazole and the like. The heteroaryl group may be substituted with one or more groups such as alkyl, substituted alkyl, and halogen. More particularly, the heteroaryl group may be substituted with methyl.

The term "subject" as used herein, refers to an animal, preferably a mammal, most preferably a human, who has been the object of treatment, observation or experiment.

Since the compounds of the invention have a chiral center, they may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulfonic, cyclohexanesulfamic, salicylic, 2-phenoxybenzoic, 2-acetoxybenzoic, saccharin, and the like. Such salts can be made by reacting the free base of compounds of formula I with the acid and isolating the salt.

Compounds of the present invention may be prepared by known methods such as those disclosed in U.S. Pat. No. 5,972,939 to Chen et al., which is hereby incorporated by reference in its entirety.

The compounds of the invention may be prepared by the following procedures. Some schemes may produce more than one embodiment of the invention. In those cases, the choice of scheme is a matter of discretion which is within the capabilities of those skilled in the art.

Essentially, Scheme 1 assembles two halves of the molecule and couples them. For one half, 3-ethoxy-2-cyclopenten-1-one, 1a (a known compound), may be the starting material. 1a can be treated with a Grignard reagent, 1b, such as 4-fluorobenzyl magnesium bromide (a known compound) preferably at room temperature (rt) under an inert atmosphere, using ether as a solvent to give the α,β-unsaturated ketone derivative 1c. Treatment of 1c with a reducing agent such as lithium aluminum hydride (LAH) preferably at 0° C. to room temperature will give the alcohol, 1d. This alcohol can be treated with a strong base such as NaH and trichloroacetonitrile preferably from 0° C. to room temperature to give the amide 1e. This six membered ring amide can be sequentially treated on dry ice with ozone, dimethylsulfide, and a catalytic amount of acid such as toluene sulfonic acid. Once addition is complete, the mixture can be warmed to room temperature to give the four membered ring aldehyde 1f, as a racemic mixture.

To assemble the other half, an aromatic alcohol 1g, such as 3-hydroxyaniline can be treated with a mild base, such as K$_2$CO$_3$, in a suitable solvent such as ethanol (EtOH) at reflux. This mixture can be subsequently treated with a halide derivative 1h, such as 3-chloropropylmorpholine preferably at room temperature to give the amine 1i. This amine can be treated with the aldehyde 1f and NaCNBH$_3$ in methanol (MeOH) preferably at room temperature to give a compound of the invention, Ic, as a racemic mixture.

If pure enantiomers are desired, they may be obtained in any of three stages of the synthesis. The alcohol 1d, the aldehyde 1f, and the product Ic may all be separated via HPLC using chiral columns or methods well known in the art. With respect to all three compounds, they may be further manipulated to give other compounds of the invention without sacrificing their enantiomeric purity.

Scheme 1 may be used to produce other compounds of the invention. For example, to produce compounds where X is sulfur, simply replace reagent 1h with an aromatic thiol, such as 3-aminothiophenol and carry out the remaining steps of the Scheme.

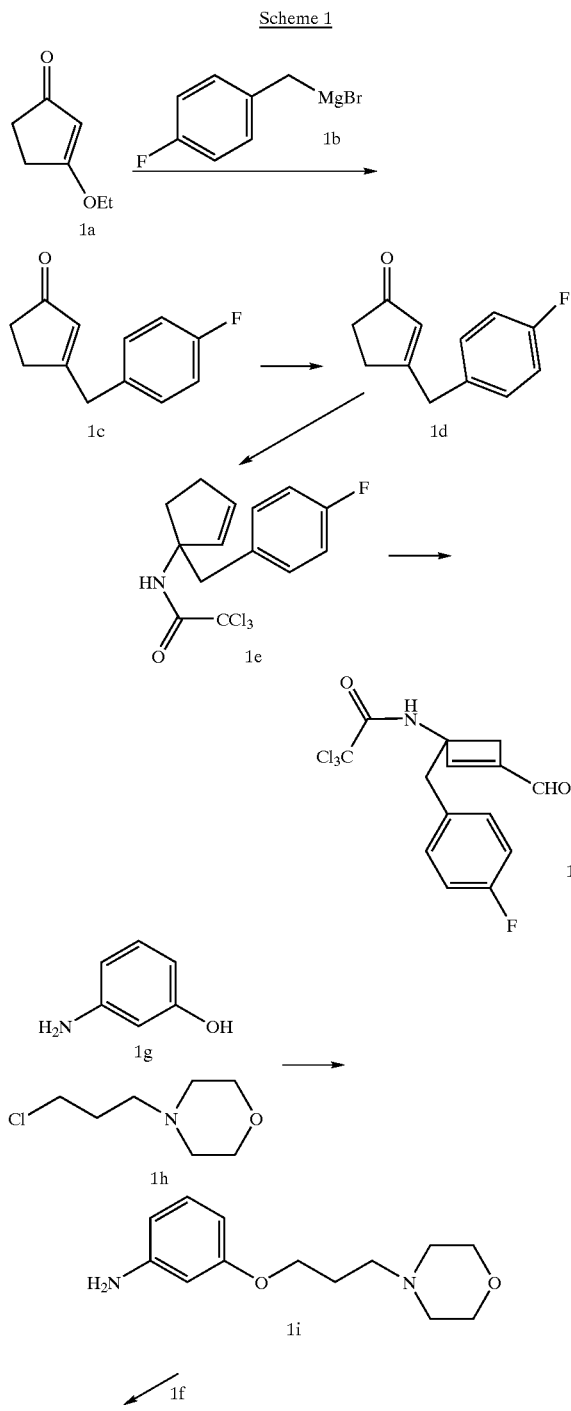

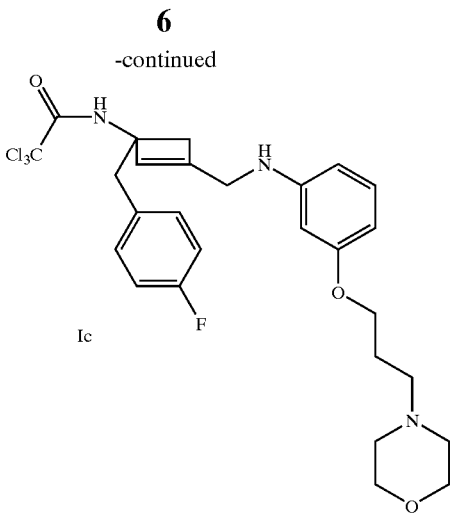

To produce other substitutions at $R_3$ or $R_4$, some of the products of Scheme 1 may be used as shown in Scheme 2. For example, to produce a compound where $R_3$ is hydrogen and $R_4$ is $CH_3C(O)$—, the five-membered ring intermediate 1e may be treated with a base, such as barium hydroxide, at reflux in ethanol to give the free amine 2a. The amine can be subsequently treated with an acid anhydride, such as trifluoroacetic anhydride, to give 2b. This intermediate may be carried through the remaining steps of Scheme 1 to

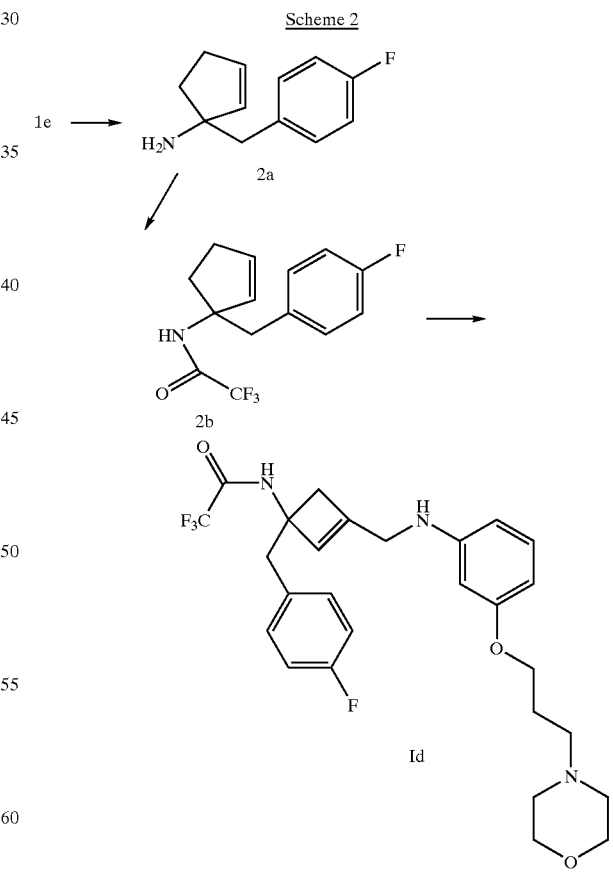

produce the desired compound Id.

The products of Scheme 1 may be used to produce other compounds of the invention as shown in Scheme 3. For example, to produce compounds of type Ie, treat compound Ic with a phenyl isocyanate preferably at room temperature. To produce compounds of type If, Ic may be treated preferably at room temperature with acid chloride derivatives such as benzoyl chloride. In order to produce thiols Ig, compounds of type Ic may be treated with isothiocyanates, such as phenylisothiocyanate preferably at room temperature. If pure enantiomers are desired, they may be obtained by chromatography of the reactant Ic or the products.

4a (a known compound), and $NaCNBH_3$ preferably at room temperature will give the coupled intermediate 4b. This intermediate may be acylated with benzoyl chloride and a mild base such as triethylamine to give the N-acyl intermediate 4c. 4c may be treated with a reducing agent such as Pd/C to give the aniline compound Ih. This compound may be coupled with a halogen derivative 4d, such as 3-chloropropylpiperidine, using DBU (1,8. Diazabicyclo

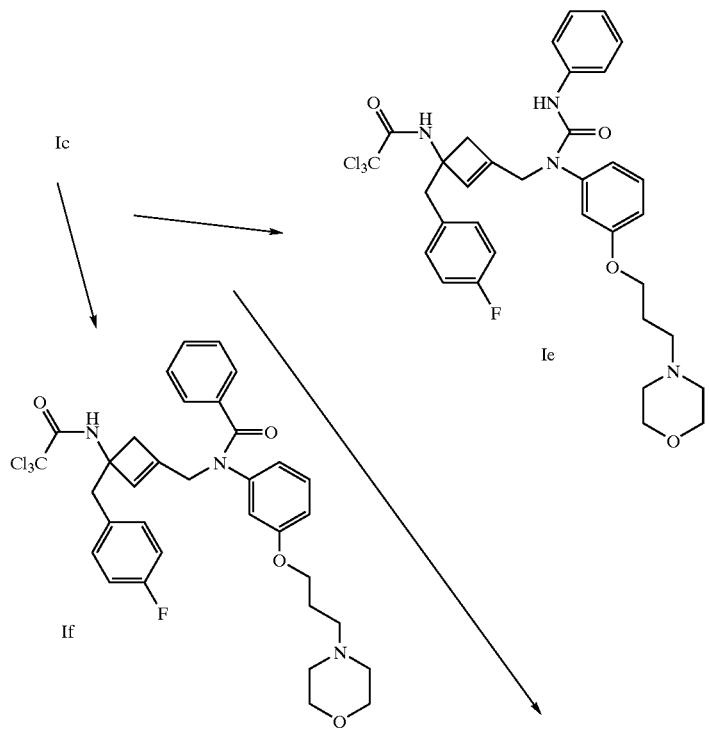

Scheme 3

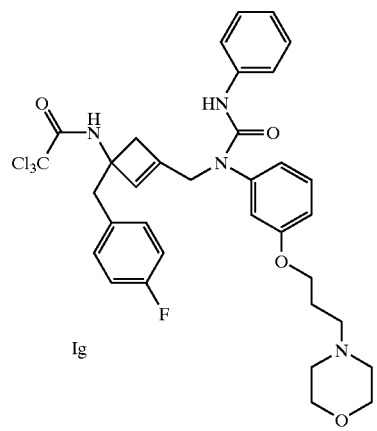

Scheme 4 makes use of the intermediate of Scheme 1. Treatment of the aldehyde, 1f, with a nitroaniline derivative (5,4,0) undec-7-ene) and an alcoholic solvent at reflux to give a mixture of mono- and di-amine products (Ii and Ij).

Scheme 4

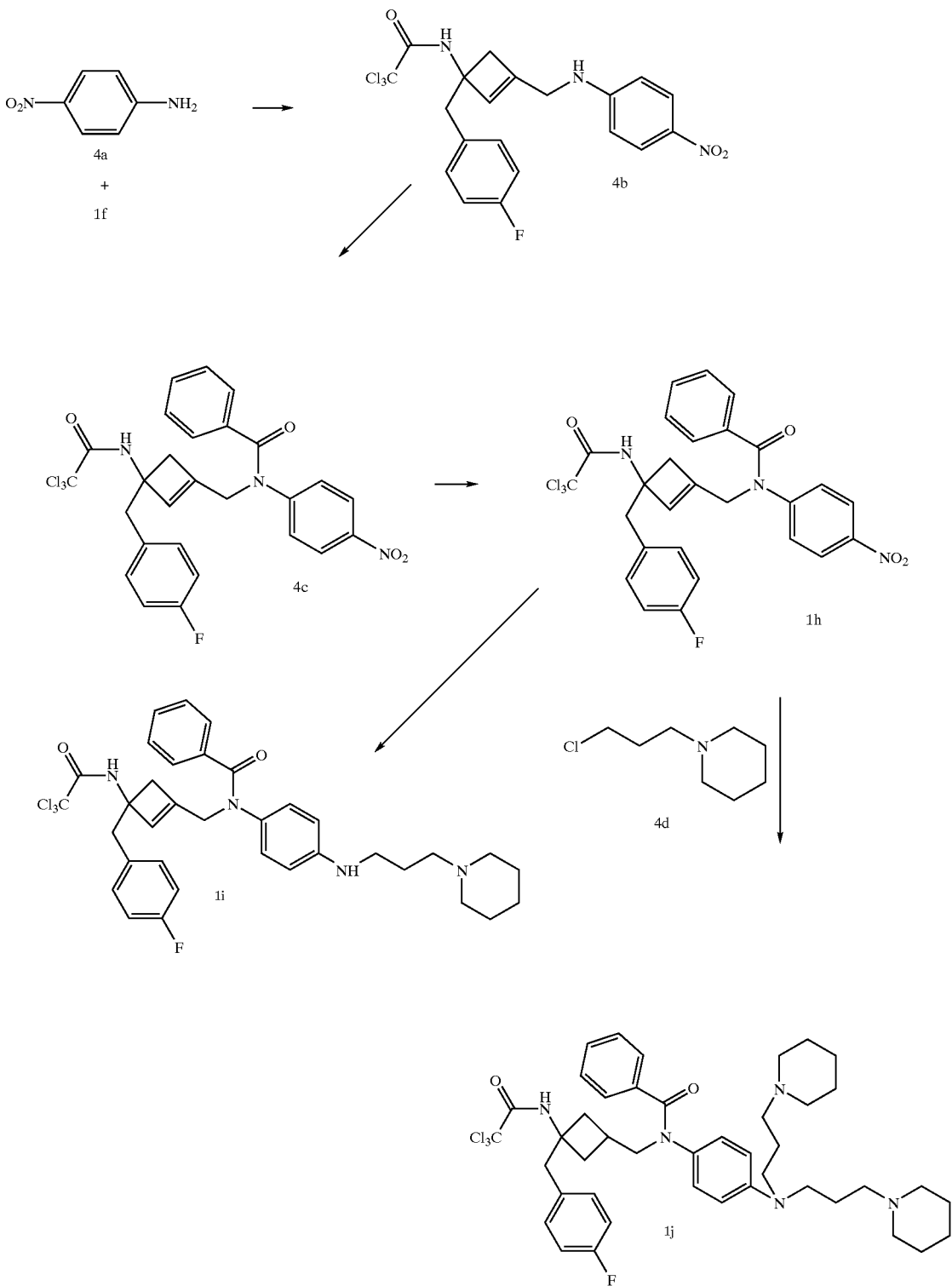

To prepare compounds of the invention where n is 1-3, products of Scheme 1 can be used as shown in Scheme 5. Intermediate 1f can be treated with 3-(m-hydroxyphenyl)propylamine, an aromatic amino alcohol derivative 5a known in the art, and NaCNBH₃ preferably at room temperature to give the amine Ik. Treatment of Ik with a thiocyanate derivative 5b, and a mild base preferably at room temperature will give the substituted thioamide Im. This compound may be treated with a halide reagent, 5c, and a base such as DBU in an alcoholic solvent at reflux to give the O-substituted compound of the invention In.

Scheme 5

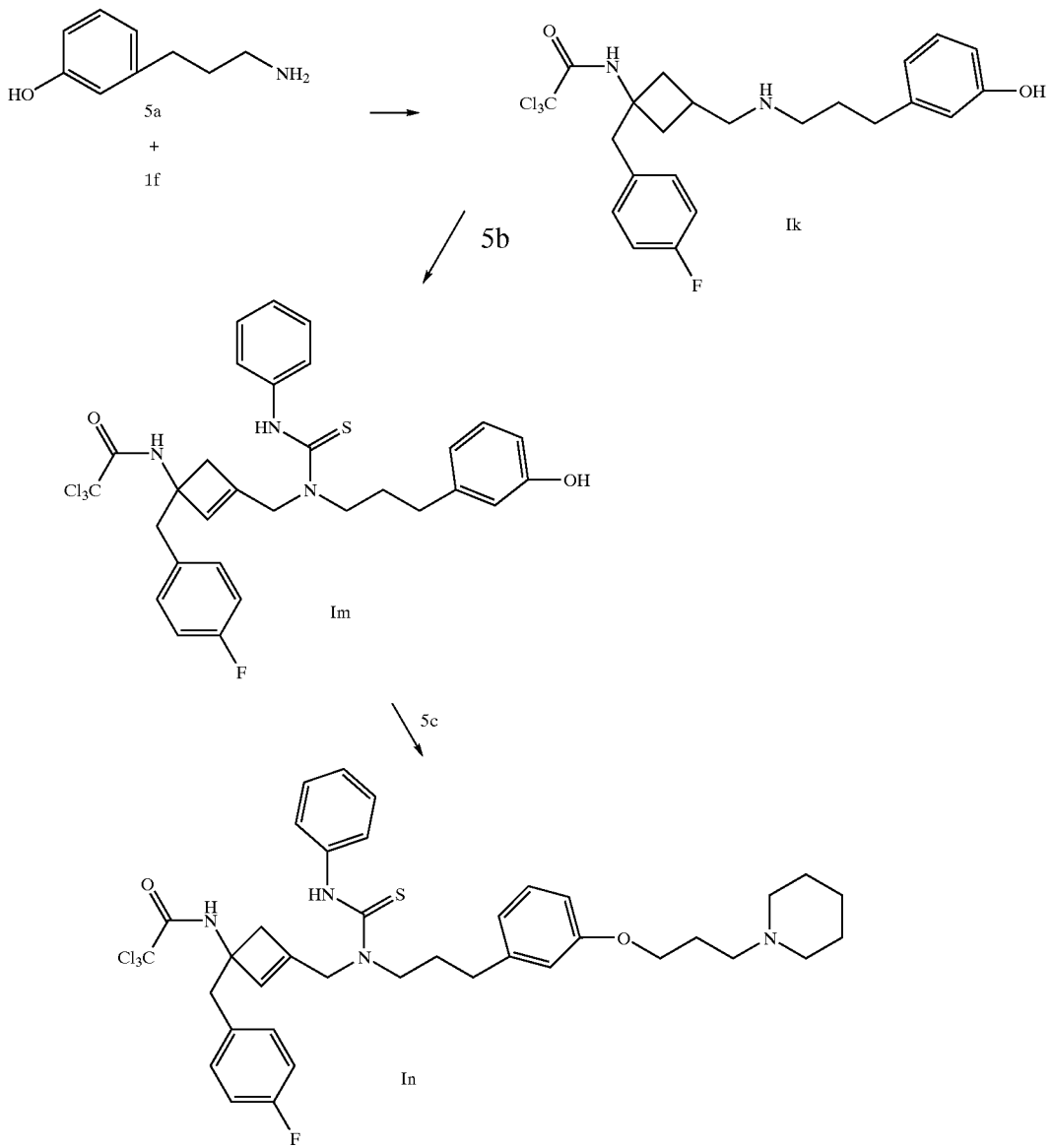

To produce compounds of the invention wherein $R_7$ and $R_8$ form sulfoxide or N-oxide, the procedure of Scheme 6 may be followed (MCPBA refers to 3-chloroperoxybenzoic acid).

Scheme 6

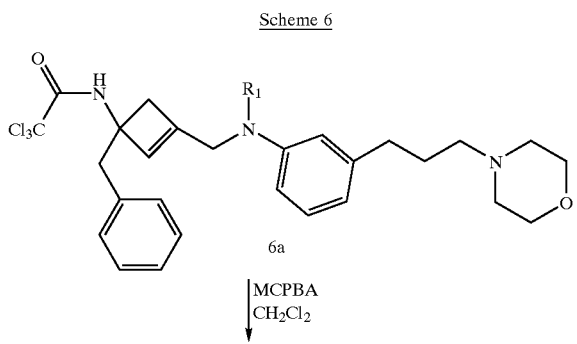

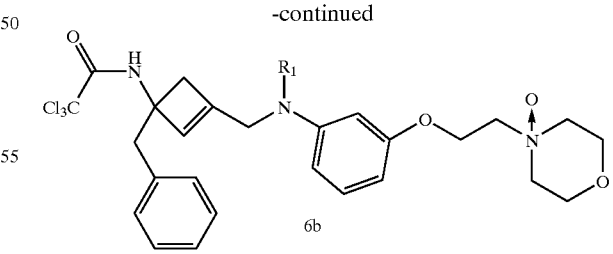

Radiolabeled Motilin

The compounds of the invention were tested for their ability to compete with radiolabeled motilin (porcine) for the motilin receptors located on the colon of mature rabbits. The colon from mature New Zealand rabbits was removed, dissected free from the mucosa and serosa layers, and diced into small pieces. The muscle tissues were homogenized in 10 volumes of buffer (50 mM Tris-Cl, 10 mM $MgCl_2$, 0.1 mg/mL bactracin, and 0.25 mM Peflabloc, pH 7.5) in a Polytron (29,000 rpm, 4×15 seconds). The homogenate was centrifuged at 1000×g for 15 min. and the supernatant discarded. The pellet was washed twice before being suspended in homogenizing buffer. This crude homogenate was then passed first through a 19 gauge needle then a 23 gauge needle to further suspend the material and stored at −80° C. In a total volume of 0.50 mL, the binding assay contained the following components added sequentially: buffer (50 mM Tris-Cl, 10 mM $MgCl_2$, 1 mM EDTA, 15 mg/mL BSA, 5 µg/mL leupeptin, aprotinin, and pepstatin, and 0.1 mg/mL, bactracin), $I^{125}$ motilin (Amersham, ca 50,000–70,000 cpm, 25–40 pM), the test compound (the initial concentration was 2 mM/100% DMSO, which was diluted with $H_2O$ to a final concentration of 10 µM) and membrane protein (100–300 µg). After 30 min at 30° C., the material was cooled on ice and centrifuged at 13,000×g for 1 minute. The pellet was washed with 1 mL 0.9% saline and centrifuged at 13,000×g for 15 seconds. The pellet was washed again with cold saline and the supernatant was removed. The pellet was counted in the gamma counter to determine the percentage of unbound motilin and thereby the percent inhibition of the test compound.

% inhibition was determined for some compounds by standard techniques:

3-Benzyl-3-trichloroacetamido-1-[N-(3,4-difluorobenzoyl)]-N-[(3-(2-morpholinoethoxy)phenyl)amino]methylcyclobutene (example 6): 14% @ 1,000 nM;

3-Benzyl-3-trichloroacetamido-1-[N-(4-bromobenzoyl)]-N-[(3-(2-morpholinoethoxy)phenyl)amino]methylcyclobutene (example 7): 47% @10,000 nM.

Rabbit Duo Denum Smooth Muscle

Compounds of the invention may be assessed for their ability to inhibit motilin and erythromycin induced contractions in the rabbit duodenum smooth muscle as follows. Rabbits may be fasted 24–48 h and euthanized. The venral midline incision may be made approximately 7.5 cm above the umbilicus up to the xyphoid process, exposing the upper peritoneal cavity. The first 8 cm of the duodenum starting at the pyloric valve may be quickly removed and placed in Krebs solution containing NaCl (120 mM), KCl (4.7 mM), $MgSO_4 \cdot 7 H_2O$ (1.2 mM), $CaCl_2 \cdot 2 H_2O$ (2.4 mM), $KH_2PO_4$ (1 mM), D-glucose (10 mM), and $NaHCO_3$ (24 mM). The lumen may be flushed with Krebs solution and excess tissue removed. The tissue may be cut lengthwise, splayed open with the longitudinal muscle layer facing up, and the longitudinal muscle layer released away from the circular muscle and cut into 3×30 mm strips. A pre-tied 4-0 silk ligature with a loop may be placed at the middle of the strip and the strip may be folded over the loop so the strip was half its original length. The tissues may be mounted in a 10 mL tissue bath (Radnotti Glass Technology, Inc., Monrovia, Calif.) containing Krebs solution gassed with 95%+$O_2$ 5% $CO_2$ at 37° C. The tissues may be attached to a force displacement transducer (FT03, Grass Instruments, Quincy, Mass.) and resting tension slowly increased to 1 g. The tissues may be allowed to equilibrate for 60–90 min with 2–3 wash cycles. The tissues may be equilibrated with two initial contractions induced by a concentration of acetylcholine (1×10$^{-4}$ M) that produce a maximal contraction (0.1 mM), with the highest taken as 100% maximal contraction of that tissue. Base line and response levels are expressed as grams tension developed and as a percent of the response to acetylcholine. The test compounds may be dissolved in DMSO (2 mM/100% DMSO) and applied to the prepared strips 5–15 minutes prior to the addition of porcine motilin. After addition, the tension is constantly monitored over 5 min and the maximum tension is recorded. The percent contraction may be measured at four ascending concentrations and where appropriate $IC_{50}$'s may be determined. The preferred compounds of the invention are those wherein:

$R_1$ is selected from phenylaminocarbonyl, substituted phenylaminocarbonyl, phenylcarbonyl, and substituted phenylcarbonyl;

$R_2$ is phenyl$C_{1-5}$alkyl, substituted phenyl$C_{1-5}$alkyl or phenyl;

$R_3$ is phenylcarbonyl, substituted phenylcarbonyl, or substituted $C_{1-5}$alkylcarbonyl;

$R_4$ is hydrogen or $C_{1-5}$alkyl;

q is 2 or 3;

A is $C_{1-5}$alkoxycarbonyl or $R_7R_8N$—wherein $R_7$ and $R_8$ are as described above;

t is 1;

n is 0; and m is 1.

In another preferred embodiment of the invention:

$R_1$ is substituted phenylcarbonyl;

$R_2$ is benzyl, 3-Cl benzyl, or 4-methoxybenzyl;

$R_3$ is substituted $C_{1-5}$alkylcarbonyl;

$R_4$ is hydrogen;

$R_6$ is hydrogen;

q is 2;

A is $R_7R_8N$—wherein $R_7$ and $R_8$ taken together form a 5 or 6 membered heterocyclic ring with one or more heteroatoms selected from the group consisting of oxygen, nitrogen, sulfur, and N-oxides thereof; and X is oxygen.

Also illustrative of the present invention is the compound of Formula I wherein:

$R_1$ is halo substituted benzoyl;

$R_3$ is halo substituted $C_{1-5}$alkylcarbonyl; and

A is morpolinyl.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use for treating disorders of the gastrointestinal system in mammals, the compounds of this invention may be administered in an amount of from about 0.5 to 100 mg/kg 1-2 times per day orally. In addition the compounds may be administered via injection at 0.1–10 mg/kg per day. Determination of optimum dosages for a particular situation is within the capabilities of formulators.

In order to illustrate the invention, the following examples are included. These examples do not limit the invention. They are meant to illustrate and suggest a method of practicing the invention. Although there are other methods of practicing this invention, those methods are deemed to be within the scope of this invention.

EXAMPLES

Example 1

3-Benzyl-2-cyclopenten-1-one

A solution of 3-ethoxy-2-cyclopenten-1-one (5 g, 0.89 mol) in THF (70 mL) was added at room temperature to a solution of 2M benzyl magnesium chloride (800 mL) under $N_2$ and stirred for 6 h. The resulting mixture was poured into a solution of 30% $H_2SO_4$ and stirred for 5 h. The resulting organic layer was separated, and the aqueous layer was extracted with several portions of ether. The combined organic layer was dried ($MgSO_4$), and concentrated in vacuo to give the title compound (3.1 g, 35%) as a colorless oil.

NMR(CDCl3):3.45(s, 2H, benzylic protons), 5.83 (bs, 1H, olefinic proton), 7.22 (m, 5H, aromatic protons).

Example 2

3-Benzyl-2-cyclopentenol

A solution of compound 3-benzyl-2-cyclopenten-1-one (3.1 g, 18 mmol) in ether (100 mL) was slowly added to a suspension of lithium aluminum hydride (LAH) (684 mg, 0.87 mol) and ether (100 mL) at 0° C. under $N_2$. The resulting mixture was stirred overnight at ambient temperature and cooled to 0° C. Saturated $K_2CO_3$ solution was added to quench the excess LAH, the mixture was filtered through Celite and washed with several portions of ether. The combined organic layers were dried ($MgSO_4$) and concentrated in vacuo to give compound the title compound (3 g, 94%) as a colorless oil.

NMR(CDCl3):3.41 (ABq, J=6 Hz, 2H, benzylic protons), 4.80 (bs, 1H, CHOH), 5.22 (bs, 1H, olefinic proton), 7.22 (m, 5H, aromatic protons).

Example 3

3-Benzyl-3-trichloroacetamidocyclopentene

A solution of compound 3-benzyl-2-cyclopentenol (3.0 g, 17.2 mmol) in ether (50 mL) was added to a suspension of hexane washed 60% NaH (468 mg, 11.7 mmol) in ether (50 mL) at 0° C. under $N_2$ and stirred for 1 h. Trichloroacetonitrile (3.0 g, 20.8 mmol) was slowly added and the resulting mixture was allowed to warm to ambient temperature and stirred overnight. The solvent was removed in vacuo, hexane (25 mL) was added and the mixture was cooled to 0° C. Methanol (1 mL) was added and the resulting solid was filtered through Celite. The organic solvent was removed in vacuo to give a crude intermediate (3.2 g). This intermediate was dissolved in xylene (0.1 L) and heated to reflux for 3 h under $N_2$. The solvent was removed in vacuo, and the residue was purified by column on silica gel (100 g, EtOAc/ hexane (1:9), to give the title compound (1.8 g, 33%) as a white crystal: mp 127–128° C.;

NMR(CDCl3):3.15 (Abq, J=7 Hz, 2H), 5.92 (m, 2H, olefinic protons), 6.60 (bs, 1H, NH), 7.22 (m, 5H, aromatic protons).

Example 4

3-Benzyl-3-trichloroacetamido-2-cyclobutenecarboxaldehyde

A solution of compound 3-benzyl-3-trichloroacetamidocyclopentene (1.01 g, 3.2 mmol) in methylene chloride (150 mL) was treated with ozone at −78° C. until the solution turned blue. The excess of ozone was removed with a stream of $N_2$, dimethyl sulfide (0.2 mL) was added and the mixture was allowed to warm to room temperature. The solvent was removed in vacuo and residue was dissolved in benzene (50 mL). TsOH—$H_2O$ (50 mg) was added and the resulting mixture was heated to reflux for 48 h. The resulting mixture was cooled to room temperature and organic layer was washed with 1 N NaOH aqueous solution and then dried. The solvent was removed in vacuo and the residue was purified by column chromatography on silica gel (EtOAc/hexane (1:9) to give the title compound (270 mg, 24%) as a thick brown oil. NMR(CDCl3):3.40 (Abq, J=8 Hz, 2H), 5.01 (m, 1H, olefinic proton), 6.85 (bs, 1H, NH), 7.22 (m, 5H, aromatic protons). 9.91 (s, 1H, CHO).

Example 5

3-Benzyl-3-trichloroacetamido-1-N-[(3-(2-morpholinoethoxy)phenyl)amino]methylcyclobutene $NaCNBH_4$ (47 mg) was added to a solution of aldehyde 3-benzyl-3-trichloroacetamido-2-cyclobutenecarboxaldehyde (230 mg, 0.69 mmol), 3-(2-morpholinoethoxy) aniline (184 mg, 0.83 mmol) acetic acid (0.05 mL) in methanol (40 mL) at room temperature under $N_2$ and stirred for 30 min. Most of methanol was removed in vacuo and the residue was diluted with methylene chloride, washed with 1N. NaOH and dried. The solvent was removed in vacuo and residue was purified by column chromatography on silica gel using ethyl acetate to give the title compound (170 mg, 45%) as a light brown oil. $MH^+$= 540.

Example 6

3-Benzyl-3-trichloroacetamido-1-[N-(3,4-difluorobenzoyl)]-N-[(3-(2-morpholinoethoxy) phenyl)amino]methylcyclobutene 3,4-Difluorobenzoyl chloride (35 mg) was added to a solution of 3-benzyl-3-trichloroactamido-1-N-[(3-(2-morpholinoethoxy)phenyl)amino]methylcyclobutene (53 mg) and triethylamine (0.3 mL) in methylene chloride (1 mL) at room temperature under $N_2$ and stirred for 2 hours. Most of solvent was removed in vacuo and the oily residue was purified by preparative TLC on silica gel using ethyl acetate as an eluent to give a light brown oil (40 mg). This oil was treated with oxalic acid in ether to give the title compound an off-white powder (25 mg, 49%): mp 90–94° C.

Example 7

3-Benzyl-3-trichloroacetamido-1-[N-(4-bromobenzoyl)]-N-[(3-(2-morpholinoethoxy)phenyl) amino]methylcyclobutene 4-Bromobenzoyl chloride (13 mg) was added to a solution of 3-benzyl-3-trichloroacetamido-1-N-[(3-(2-morpholinoethoxy)phenyl)amino]methylcyclobutene (20 mg) and triethylamine (0.3 mL) in methylene chloride (1 mL) at room temperature under $N_2$ and stirred for 2 hours. Most of solvent was removed in vacuo and the oily residue was purified by preparative TLC on silica gel using ethyl acetate as an eluent to give a light brown oil (12 mg). This oil was treated with oxalic acid in ether to give the title compound) as an off-white powder (7 mg, 49%). MS (MH+=722).

What is claimed is:

1. A method of treating disorders associated with the motilin receptor in humans comprising administering to a subject an effective amount of a compound of Formula (I):

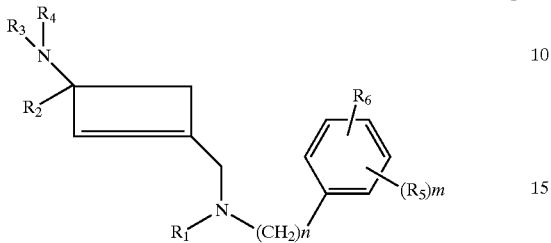

wherein
- $R^1$ is selected from hydrogen, $C_{1-5}$alkyl optionally substituted with halogen, amino$C_{1-5}$alkyl, $C_{1-5}$alkylamino$C_{1-5}$alkyl, di-$C_{1-5}$alkylamino$C_{1-5}$alkyl, $C_{1-5}$alkylcarbonyl, $C_{1-5}$alkoxycarbonyl, aminocarbonyl, $C_{1-9}$alkylaminocarbonyl, cyclo$C_{3-9}$alkylaminocarbonyl, heteroarylaminocarbonyl optionally substituted with one or more $C_{1-5}$alkyl, pyridinylcarbonyl optionally substituted with one or more substituents selected from the group consisting of halogen and $C_{1-5}$alkyl, thiophenecarbonyl optionally substituted with one or more substituents selected from the group consisting of halogen and $C_{1-5}$alkyl, phenyl, phenyl$C_{1-5}$alkyl, phenoxycarbonyl, phenylcarbonyl, diphenylmethylcarbonyl, phenylaminocarbonyl, phenylthiocarbonyl, phenylaminothiocarbonyl, said phenyl, phenyl$C_{1-5}$alkyl, phenoxycarbonyl, phenylcarbonyl, diphenylmethylcarbonyl, phenylaminocarbonyl, phenylthiocarbonyl, phenylaminothiocarbonyl being optionally substituted with one or more substituents selected from the group consisting of halogen, $C_{1-5}$alkyl, trihalomethyl, $C_{1-5}$alkoxy, amino, nitrile, nitro, $C_{1-5}$alkylamino, and di-$C_{1-5}$alkylamino, which substituents may be taken together to form a fused bicyclic aromatic ring or taken together with the phenyl ring to form a fused bicyclic 7–10 membered heterocyclic ring having one or two heteroatoms selected from oxygen, sulfur and nitrogen, and $R_aR_bN$—$C_{1-5}$alkyl wherein $R_a$ and $R_b$ are independently selected from hydrogen and $C_{1-5}$alkyl, or taken together to form a morpholine, piperazine, piperidine, or N-substituted piperidine wherein the N-substitutent is $C_{1-5}$alkyl or phenyl$C_{1-5}$alkyl;
- $R_2$ is selected from hydrogen, $C_{1-5}$alkyl, $C_{1-5}$alkoxy, phenyl optionally substituted with one or more substituents selected from the group consisting of halogen and $C_{1-5}$alkyl, and phenyl$C_{1-5}$alkyl optionally substituted with one or more substituents selected from the group consisting of halogen, $C_{1-5}$alkyl, $C_{1-5}$alkoxy, halo and di-$C_{1-5}$alkylamino;
- $R_3$ is selected from hydrogen, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;
- $R_4$ is selected from hydrogen, $C_{1-5}$alkyl, $C_{1-5}$alkylcarbonyl optionally substituted with halogen, and phenylcarbonyl optionally substituted with one or more substituents selected from the group consisting of halogen, $C_{1-5}$alkyl, $C_{1-5}$alkoxy, amino, $C_{1-5}$alkylamino, and di-$C_{1-5}$alkylamino;
- n is 0–3;
- m is 1–5;
- $R_5$ is

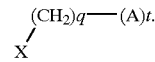

wherein:
- q is 0–3;
- t is 0–1;
- X is oxygen, $CH_2$, sulfur, hydroxy, thiol, or $NR_c$ wherein
  - $R_c$ is selected from hydrogen, $C_{1-5}$alkyl, morpholino$C_{1-5}$alkyl, piperidinyl$C_{1-5}$alkyl, N-phenylmethylpiperidinyl, and piperazinyl$C_{1-5}$alkyl,
- with the proviso that if q and t are 0, X is hydroxy, thiol, or amino;
- A is $C_{1-5}$alkoxycarbonyl, phenylcarbonyl, or $R_7R_8N$- wherein $R_7$ and $R_8$ are independently selected from hydrogen, $C_{1-5}$alkyl, and cyclo$C_{1-9}$alkyl, or $R_7$ and $R_8$ form a 5- or 6-membered heterocyclic ring with one or more heteroatoms selected from the group consisting of oxygen, nitrogen, sulfur, and sulfoxides and N-oxides thereof; and
- $R_6$ is selected from hydrogen, halogen, $C_{1-5}$alkoxy, $C_{1-5}$alkylamino, and di-$C_{1-5}$alkylamino;
or a pharmaceutically acceptable salt thereof.

2. A method of claim 1, wherein the disorder is irritable bowel syndrome or esophageal reflux.

3. A method of claim 1, wherein the compound is a compound of Formula (I)

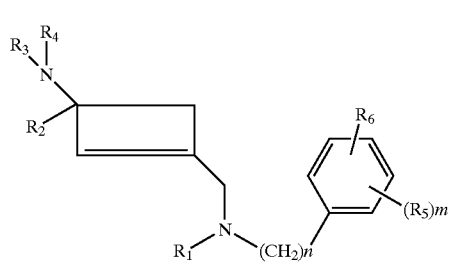

wherein
- $R_1$ is selected from phenylaminocarbonyl, substituted phenylaminocarbonyl, phenylcarbonyl, and substituted phenylcarbonyl;
- $R_2$ is phenyl$C_{1-5}$alkyl, substituted phenyl$C_{1-5}$alkyl or phenyl;
- $R_3$ is phenylcarbonyl, substituted phenylcarbonyl, or substituted $C_{1-5}$alkylcarbonyl;
- $R_4$ is hydrogen or $C_{1-5}$alkyl;
- q is 2 or 3;
- A is $C_{1-5}$alkoxycarbonyl or $R_7R_8N$- wherein $R_7$ and $R_8$ are
  - wherein $R_7$ and $R_8$ are independently selected from hydrogen, $C_{1-5}$alkyl, and cyclo$C_{1-9}$alkyl, or $R_7$ and $R_8$ form a 5- or 6-membered heterocyclic ring with one or more heteroatoms selected from the group consisting of oxygen, nitrogen, sulfur, and sulfoxides and N-oxides thereof; and t is 1;

n is 0; and m is 1.

4. A method of claim 1, wherein the compound is a compound of Formula (I)

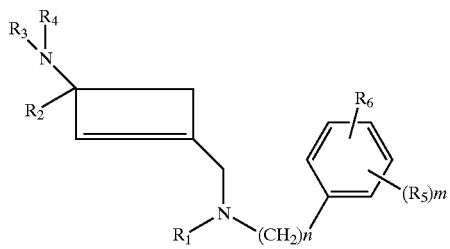

wherein

R$_1$ is substituted phenylcarbonyl;

R$_2$ is benzyl, 3-Cl benzyl, or 4methoxybenzyl;

R$_3$ is substituted C$_{1-5}$alkylcarbonyl;

R$_4$ is hydrogen;

R$_6$ is hydrogen;

q is 2;

A is R$_7$R$_8$N- wherein R$_7$ and R$_8$ taken together form a 5 or 6 membered heterocyclic ring with one or more heteroatoms selected from the group consisting of oxygen, nitrogen, sulfur, and N-oxides thereof; and X is oxygen.

5. A method of claim 1, wherein the compound is a compound of Formula (Ia) or (Ib)

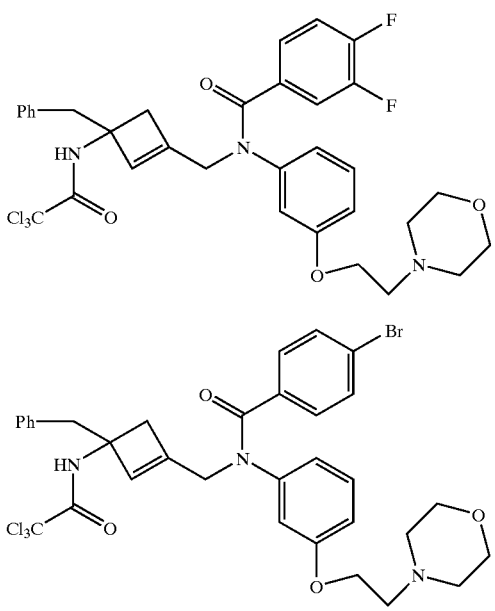

6. A method of treating a gastrointestinal side effect resulting from administration of erythromycin, which comprises administering to a subject an effective amount of a compound of Formula (I):

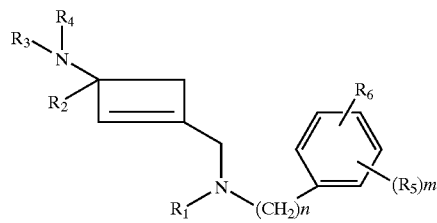

wherein

R$_1$ is selected from hydrogen, C$_{1-5}$alkyl optionally substituted with halogen, aminoC$_{1-5}$alkyl, C$_{1-5}$alkylaminoC$_{1-5}$alkyl, di-C$_{1-5}$alkylaminoC$_{1-5}$alkyl, C$_{1-5}$alkylcarbonyl, C$_{1-5}$alkoxycarbonyl, aminocarbonyl, C$_{1-9}$alkylaminocarbonyl, cycloC$_{3-9}$alkylaminocarbonyl, heteroarylaminocarbonyl optionally substituted with one or more C$_{1-5}$alkyl, pyridinylcarbonyl optionally substituted with one or more substituents selected from the group consisting of halogen and C$_{1-5}$alkyl, thiophenecarbonyl optionally substituted with one or more substituents selected from the group consisting of halogen and C$_{1-5}$alkyl, phenyl, phenylC$_{1-5}$alkyl, phenoxycarbonyl, phenylcarbonyl, diphenylmethylcarbonyl, phenylaminocarbonyl, phenylthiocarbonyl, phenylaminothiocarbonyl, said phenyl, phenylC$_{1-5}$alkyl, phenoxycarbonyl, phenylcarbonyl, diphenylmethylcarbonyl, phenylaminocarbonyl, phenylthiocarbonyl, phenylaminothiocarbonyl being optionally substituted with one or more substituents selected from the group consisting of halogen, C$_{1-5}$alkyl, trihalomethyl, C$_{1-5}$alkoxy, amino, nitrile, nitro, C$_{1-5}$alkylamino, and di-C$_{1-5}$alkylamino, which substituents may be taken together to form a fused bicyclic aromatic ring or taken together with the phenyl ring to form a fused bicyclic 7–10 membered heterocyclic ring having one or two heteroatoms selected from oxygen, sulfur and nitrogen, and R$_a$R$_b$N—C$_{1-5}$alkyl wherein R$_a$ and R$_b$ are independently selected from hydrogen and C$_{1-5}$alkyl, or taken together to form a morpholine, piperazine, piperidine, or N-substituted piperidine wherein the N-substitutent is C$_{1-5}$alkyl or phenylC$_{1-5}$alkyl;

R$_2$ is selected from hydrogen, C$_{1-5}$alkyl, C$_{1-5}$alkoxy, phenyl optionally substituted with one or more substituents selected from the group consisting of halogen and C$_{1-5}$alkyl, and phenylC$_{1-5}$alkyl optionally substituted with one or more substituents selected from the group consisting of halogen, C$_{1-5}$alkyl, C$_{1-5}$alkoxy, halo and di-C$_{1-5}$alkylamino;

R$_3$ is selected from hydrogen, C$_{1-5}$alkylcarbonyl optionally substituted with halogen, and phenylcarbonyl optionally substituted with one or more substituents selected from the group consisting of halogen, C$_{1-5}$alkyl, C$_{1-5}$alkoxy, amino, C$_{1-5}$alkylamino, and di-C$_{1-5}$alkylamino;

R$_4$ is selected from hydrogen, C$_{1-5}$alkyl, C$_{1-5}$alkylcarbonyl optionally substituted with halogen, and phenylcarbonyl optionally substituted with one or more substituents selected from the group consisting of halogen, C$_{1-5}$alkyl, C$_{1-5}$alkoxy, amino, C$_{1-5}$alkylamino, and di-C$_{1-5}$alkylamino;

n is 0–3;

m is 1–5;

$R_5$ is $$\underset{X}{\diagup}(CH_2)_q-(A)_t$$

wherein:
q is 0–3;
t is 0–1;
X is oxygen, $CH_2$, sulfur, hydroxy, thiol, or $NR_c$ wherein
$R_c$ is selected from hydrogen, $C_{1-5}$alkyl, morpholino$C_{1-5}$alkyl, piperidinyl$C_{1-5}$alkyl, N-phenylmethylpiperidinyl, and piperazinyl$C_{1-5}$alkyl,
with the proviso that if q and t are 0, X is hydroxy, thiol, or amino;
A is $C_{1-5}$alkoxycarbonyl, phenylcarbonyl, or $R_7R_8N$- wherein $R_7$ and $R_8$ are independently selected from hydrogen, $C_{1-5}$alkyl, and cyclo$C_{1-9}$alkyl, or $R_7$ and $R_8$ form a 5- or 6-membered heterocyclic ring with one or more heteroatoms selected from the group consisting of oxygen, nitrogen, sulfur, and sulfoxides and N-oxides thereof; and
$R_6$ is selected from hydrogen, halogen, $C_{1-5}$alkoxy, $C_{1-5}$alkylamino, and di-$C_{1-5}$alkylamino;
or a pharmaceutically acceptable salt thereof.

7. A method of claim 6, wherein the gastrointestinal side effect is irritable bowel syndrome or esophageal reflux.

8. A method of claim 6, wherein the compound is a compound of Formula (I)

I wherein
$R_1$ selected from phenylaminocarbonyl, substituted phenylaminocarbonyl, phenylcarbonyl, and substituted phenylcarbonyl;
$R_2$ is phenyl$C_{1-5}$alkyl, substituted phenyl$C_{1-5}$alkyl or phenyl;
$R_3$ is phenylcarbonyl, substituted phenylcarbonyl, or substituted $C_{1-5}$alkylcarbonyl;
$R_4$ is hydrogen or $C_{1-5}$alkyl;
q is 2 or 3;
A is $C_{1-5}$alkoxycarbonyl or $R_7R_8N$- wherein $R_7$ and $R_8$ are wherein $R_7$ $R_8$ are independently selected from hydrogen, $C_{1-5}$alkyl, and cyclo$C_{1-9}$alkyl, or $R_7$ and $R_8$ form a 5- or 6-membered heterocyclic ring with one or more heteroatoms selected from the group consisting of oxygen, nitrogen, sulfur, and sulfoxides and N-oxides thereof; and;

t is 1;
n is 0; and
m is 1.

9. A method of claim 6, wherein the compound is a compound of Formula (I)

I wherein
$R_1$ is substituted phenylcarbonyl;
$R_2$ is benzyl, 3-Cl benzyl, or 4-methoxybenzyl;
$R_3$ is substituted $C_{1-5}$alkylcarbonyl;
$R_4$ is hydrogen;
$R_6$ is hydrogen;
q is 2;
A is $R_7R_8N$- wherein $R_7$ and $R_8$ taken together form a 5 or 6 membered heterocyclic ring with one or more heteroatoms selected from the group consisting of oxygen, nitrogen, sulfur, and N-oxides thereof; and
X is oxygen.

10. A method of claim 6, wherein the compound is a compound of Formula (Ia) or (Ib)

Ia

Ib

* * * * *